US008222449B2

(12) United States Patent
Stewart et al.

(10) Patent No.: US 8,222,449 B2
(45) Date of Patent: Jul. 17, 2012

(54) METAL OXIDE-CHELATING LIGANDS

(75) Inventors: Michael Stewart, Washington, DC (US); Kimihiro Susumu, Alexandria, VA (US); Dorothy Farrell, Alexandria, VA (US); Hedi M. Mattoussi, Tallahassee, FL (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/962,988

(22) Filed: Dec. 8, 2010

(65) Prior Publication Data

US 2011/0137079 A1    Jun. 9, 2011

Related U.S. Application Data

(60) Provisional application No. 61/267,477, filed on Dec. 8, 2009.

(51) Int. Cl.
*C07C 229/24* (2006.01)
(52) U.S. Cl. ....................................... 562/568
(58) Field of Classification Search .................. None
See application file for complete search history.

(56) References Cited

U.S. PATENT DOCUMENTS

| 4,956,267 | A  | 9/1990 | Ueda et al. |
| 7,160,613 | B2 | 1/2007 | Bawendi et al. |
| 7,361,516 | B2 | 4/2008 | Uyeda et al. |
| 7,648,843 | B2 | 1/2010 | Uyeda et al. |

FOREIGN PATENT DOCUMENTS

JP     63261362 A     10/1988

OTHER PUBLICATIONS

Voit, Acta Polymerica, Dendritic Polymers : From Aesthetic Molecules to Commercially Interesting Materials, 1995, 46, pp. 87-99.*
Zhou et al, Organic and Biomoelecular Chemistry, Cooperative Binding and Self-assembling Behavior of Cationic Low Molecular-weight Dendrons with RNA Molecules, 2006, 4 pp. 581-585.*
Bouillon et al., "Efficient synthesis of esters containing tertiary amine functionalities via active cyanomethyl ester intermediates" Tetrahedron Lett., 50, 4346-4349 (2009).
Kim et al., "Oligomeric Ligands for Luminescent and Stable Nanocrystal Quantum Dots" J. Am. Chem. Soc., 125, 14652-14653 (2003).
Mei et al., "Modular poly(ethylene glycol) ligands for biocompatible semiconductor and gold nanocrystals with extended pH and ionic stability" J. Mater. Chem., 18, 4949-4958 (2008).
Park et al., "Ultra-large-scale syntheses of monodisperse nanocrystals" Nat. Mater., 3, 891-895 (2004).
Sashiwa et al., "Chemical modification of chitosan 11: chitosan-dendrimer hybrid as a tree like molecules" Carbohydrate Polymers, 49, 195-205 (2002).
Sashiwa et al., "Synthesis of chitosan-dendrimer hybrid" Advances in Chitin Science, 5, 273-277 (2002) (abstract).
Susumu et al., "Enhancing the Stability and Biological Functionalities of Quantum Dots via Compact Multifunctional Ligands" J. Am. Chem. Soc., 129, 13987-13996 (2007).
Uyeda et al., "Synthesis of Compact Multidentate Ligands to Prepare Stable Hydrophilic Quantum Dot Fluorophores" J. Am. Chem. Soc., 127, 3870-3878 (2005).
Wan et al., "Biocompatible superparamagnetic iron oxide nanoparticledispersions stabilized with poly(ethylene glycol)-oligo(aspartic acid) hybrids" J. Biomed. Mater. Res. Part A, 80A, 946-954 (2006).
Xie et al., "Controlled PEGylation of Monodisperse Fe3O4 Nanoparticles for Reduced Non-Specific Uptake by Macrophage Cells" Adv. Mater, 19, 3163-3166 (2007).

* cited by examiner

*Primary Examiner* — Paul A Zucker
(74) *Attorney, Agent, or Firm* — Amy L. Ressing; Joseph T. Grunkemeyer

(57) ABSTRACT

Compounds having the formulas below. The values n and x are independently selected positive integers.

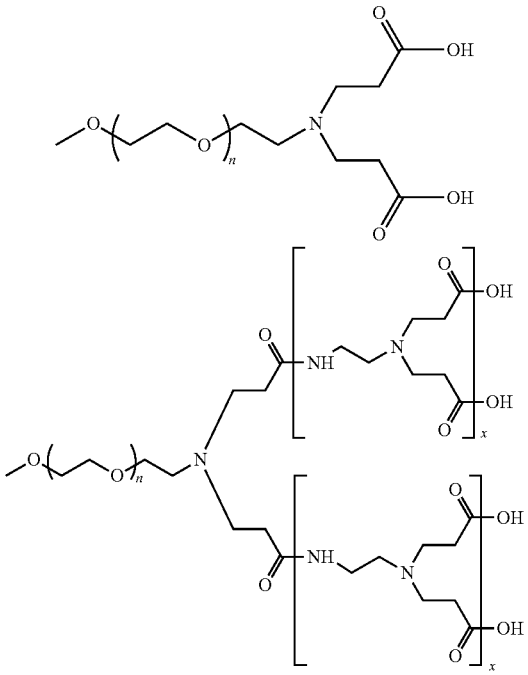

6 Claims, 3 Drawing Sheets

METAL OXIDE-CHELATING LIGANDS

This application claims the benefit of U.S. Provisional Application No. 61/267,477, filed on Dec. 8, 2009. The provisional application and all other publications and patent documents referred to throughout this nonprovisional application are incorporated herein by reference.

TECHNICAL FIELD

The present disclosure is generally related to ligands for chelating metal oxides.

DESCRIPTION OF RELATED ART

The use of multidentate PEGylated ligands (PEG=polyethylene glycol) for the water solubilisation of quantum dots and gold nanoparticles across a range of pH values and ionic strengths has been reported (Uyeda et al., *J. Am. Chem. Soc.*, 127, 3870 (2005)). Via cap exchange, native hydrophobic ligands are replaced with PEG-based ligands bearing dihydrolipoic acid headgroups. By using multiple headgroups in the ligand, stability can be imparted even at acidic pH and high ionic strength.

Thiol groups, while providing strong interaction to both semiconductor and Au surfaces, exhibit very weak interactions with metal oxides and are thus not effective for magnetic iron oxide nanoparticles. Carboxylic acid groups exhibit strong affinity to metal oxide surfaces, and carboxylic acid terminated hydrocarbons are standard surfactants used in the synthesis of high quality, uniform ferrite nanoparticles at high temperature in non-polar solvents (Park et al., *Nature Mat.*, 3, 891 (2004)). However, as with all the metal-coordinating groups, a single carboxylic acid terminal group provides only limited stability to iron oxide nanoparticles in aqueous solutions. Iron oxide nanoparticles have been synthesized in water and coated with co-polymers containing multiple carboxylic acid groups, such as oligo-aspartic acid (Wan et al., *J. Biomed. Mat. Res Part A*, 80A, 946 (2007)) or polyurethane (Harris et al., *Chem. Mater.*, 15, 1367 (2003)), to render them biocompatible. However, these particles are not highly uniform in size and shape, and the co-polymer coating can be quite large. Water solubilisation of high quality, hydrophobic magnetic nanoparticles can be achieved through encapsulation within phospholipid micelles using commercially available (1,2-distearoyl-sn-glycero-3-phophoethanol-amine-N-amino-poly(ethylene glycol), DSPE-PEG 2000 amine (Nitin et al., *J. Biol. Inorg Chem.*, 9, 706 (2004)). This approach results in a relatively small (3-4 nm) coating, and the particles are stable in biological fluid, but long term stability depends on the integrity of the micelles. Cap-exchange with molecular scale ligands promises to provide nanoparticles with small to no size increase compared to their native state, and when combined with multi-coordinating end groups (2, 3, 4, . . . carboxylic acids) it can provide compact magnetic nanoparticles that are stable over a broad range of biologically relevant conditions.

Iron oxide nanoparticles have been water solubilized via cap exchange with hydrophilic ligands or polymers having a terminal dopamine (catechol) end group (Xu et al., *J. Am Chem. Soc.*, 126, 9938 (2004); Xie et al., *Adv. Mat.*, 19, 3163 (2007)). Although compact and dispersible in phosphate buffered saline solution, a surrogate for physiologic fluid, these particles are not stable at pH 6 and below. Some intracellular compartments may have pH as low as 3-4, making these particles unsuitable for some cellular studies. Also of concern is the reactive nature of the catechol-iron bond, which leads to corrosion of the particle surface, resulting in changes in particle shape and size (Xie et al., *Chem. Mater.*, 18, 5401 (2006); Shultz et al., *J. Am. Chem. Soc.*, 129, 2482 (2007)). Such corrosion can result in degradation of the magnetic properties of the particles over time.

BRIEF SUMMARY

Disclosed herein are compounds having the formulas in Eqs. (1) and (2). The values n and x are independently selected positive integers.

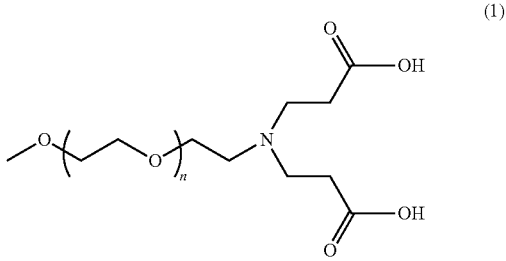

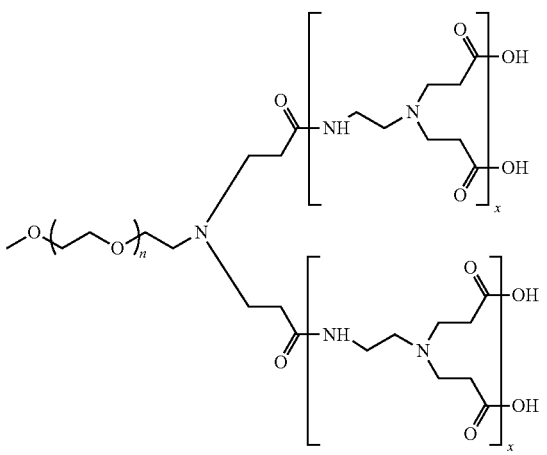

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Figure 1:
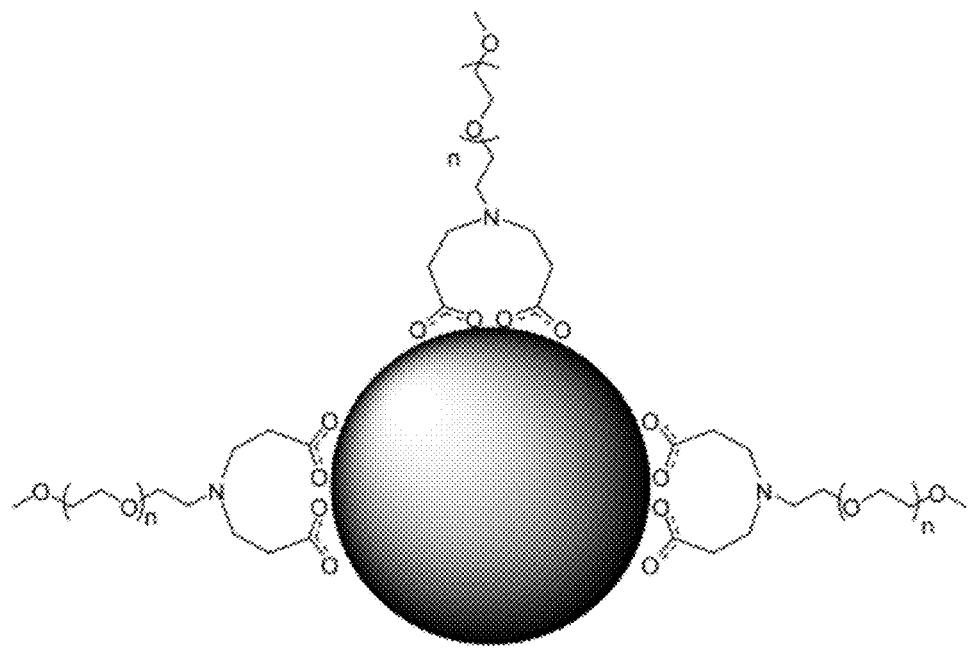
FIG. 1 shows water-soluble nanoparticles prepared with the bi-carboxylic acid PEG ligand C.

Disclosed herein is the synthesis of a poly(ethylene glycol) based ligand terminating in multiple carboxylic acid functional groups, and its use to cap metal oxide (magnetic) nanoparticles and promote their transfer to aqueous media. The surface ligands each consist of a tuneable length PEG chain, which provides water solubility to the nanoparticles, two (or more) carboxylic acid terminal groups at one end for anchoring on the nanocrystal, and a potentially reactive group at the opposite end of the PEG for coupling to other target molecules such as bioreceptors, as shown in FIG. 1. Carboxylic acid bind to the iron oxide surface via a Lewis acid-base interaction (point coordination) and this "bond" is by nature rather weak. Thus mono-dentate interactions tend to produce nanoparticles with limited stability both to added salts and pH variations. Appending multi-coordinating groups (in one anchoring head) to the ligand provides nanoparticles that are stable in phosphate buffered saline (PBS) solutions and over a broad range of pH values ($4 \leq pH \leq 11$). The other end of the PEG chain can be functionalized for easy attachment to desired targets. For example, using an azide can allow coupling through click chemistry to alkyne functionalized particles or molecules, while biotin groups could allow coupling via biotin-avidin bridging. Conjugation of the magnetic nanoparticles with biologically relevant materials will allow targeting (using proteins or peptides) or imaging (using dyes or optically active particles) of cells or tissue. These conjugates could also enable the creation of multifunctional platforms with combined diagnostic and therapeutic capacities.

Figure 2:
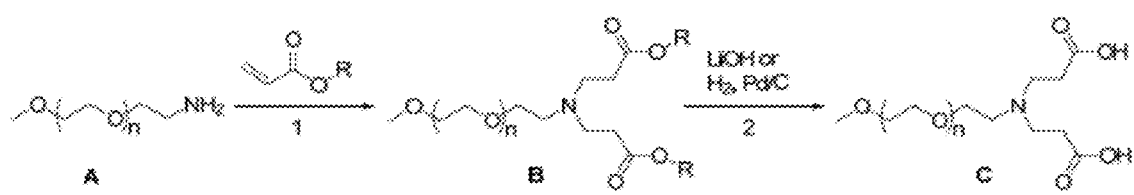
FIG. 2 shows a synthesis of a bi-carboxylic acid PEG ligand.

The preparation of the bi-carboxylic acid ligand is shown in FIG. 2. First, commercially available poly(ethylene glycol) methyl ether (MPEG) is functionalized with an amine group (compound A) as disclosed by Mei et al., *J. Mater. Chem.*, 18, 4949-4958 (2008). Suitable values for n include, but are not limited to, integers greater than or equal to 1, 2, 3, 4, 5, 10, 15, 20, and 100. Compound A is then converted to compound B via Michael addition with methyl acrylate ($R=CH_3$) or benzyl acrylate ($R=CH_2C_6H_5$), yielding an MPEG chain terminating in a pair of R-protected carboxylate groups, as disclosed by Pittelkow et al., *Org. Lett.*, 7, 1295 (2005). Deprotection via reduction with LiOH ($R=CH_3$) or hydrogenation in the presence of palladium catalyst ($R=CH_2C_6H_5$) affords the final product (compound C), containing two carboxylate groups. This product is then washed with ethyl acetate to yield $(COOH)_2$-PEG-$OCH_3$. This ligand was shown to be a suitable capping agent for iron oxide nanoparticles.

Figure 3:
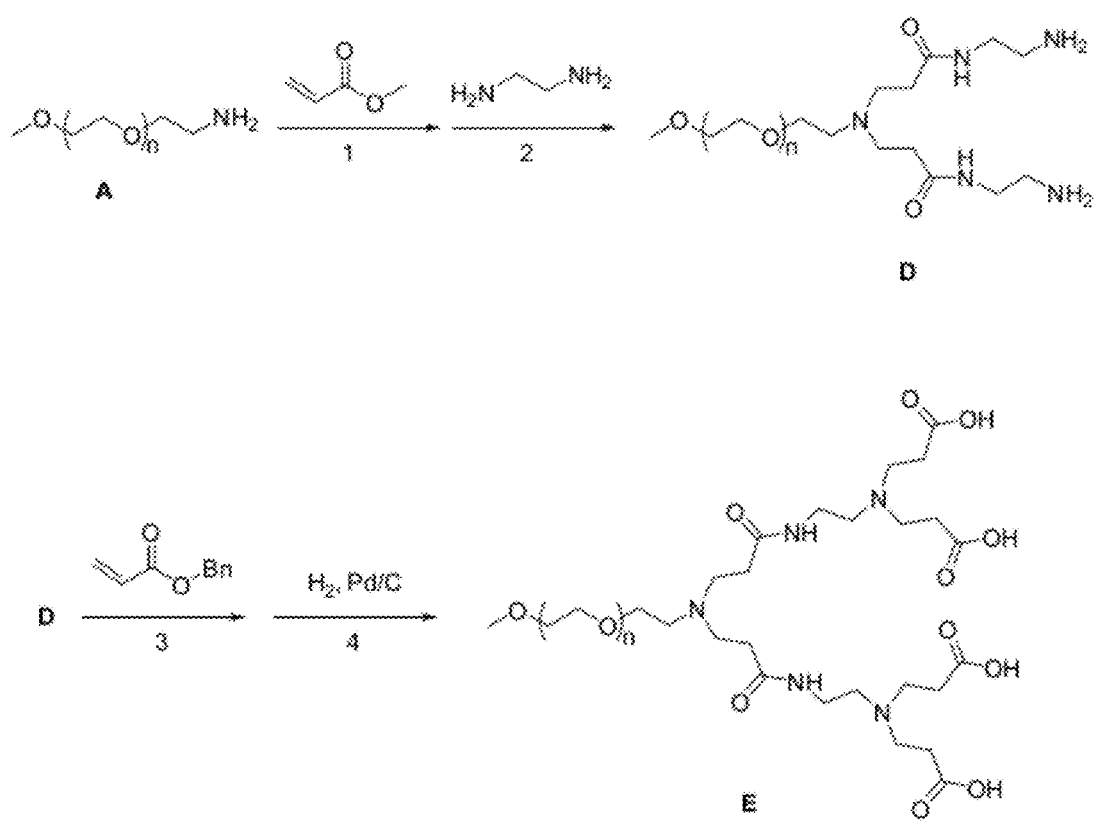
FIG. 3 shows the preparation of multi-carboxylic acid PEG ligands.

This methodology may be extended to the synthesis of ligands bearing $2^m$ carboxylic acid end-groups, as shown in FIG. 3. First, compound A is treated with methyl acrylate to form the Michael addition product, which is then treated with excess ethylene diamine to yield $(NH_2)_2$-PEG-$OCH_3$ (compound D). Each amine group of D may then be converted to two carboxylic acid groups using the reactions outlined in FIG. 1 to afford the multi-carboxylic acid ligand E. The sequence outlined in FIG. 3 yields a PEG ligand (E) functionalized with 4 carboxylic acid groups ($2^m$, m=2). Intermediate D was isolated and characterized using $^1H$ NMR.

The ligands synthesized in these reactions were used to transfer hydrophobic iron oxide nanoparticles into aqueous solution. The initial, oleic acid coated iron oxide particles were precipitated from non-polar organic solvent via addition of ethanol and centrifugation or magnetic separation. The PEG ligand was then added to the precipitate along with methanol. The system was then sonicated to disperse the pelleted iron oxide and placed in an oil bath at 60-70° C. for 16-20 hours. The particles were then precipitated using a mixture of ethanol, chloroform and hexanes, redispersed in deionized water, centrifuged in a filter tube (50 kDa cutoff) to remove excess ligand and passed through a 0.45 μm PTFE filter. The resulting solution is stable in water or neutral or alkaline PBS for more than two months, and in PBS buffer solutions at pH$\geq$4 for more than 2 weeks.

Figure 4:
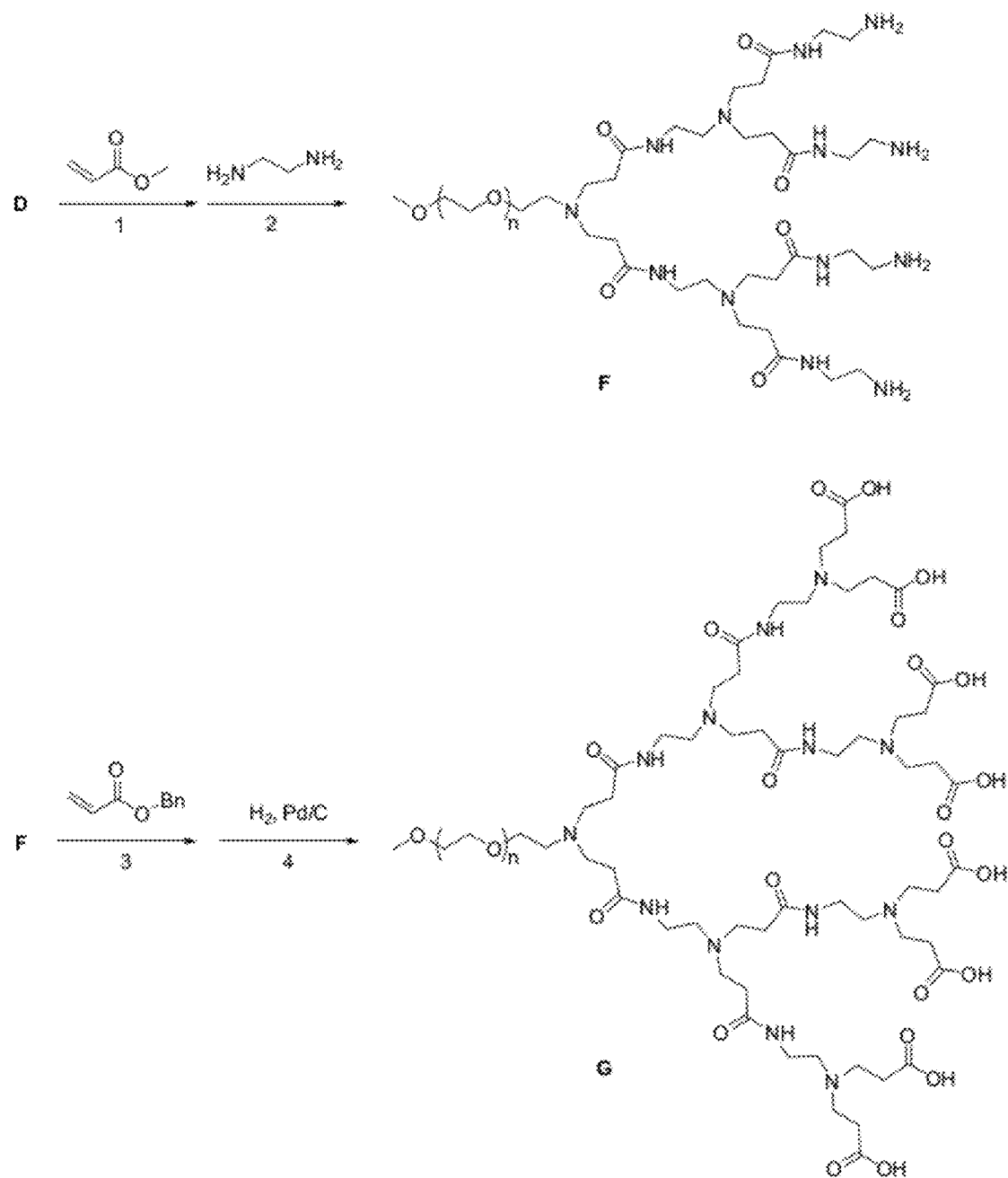
FIG. 4 shows a PEG ligand with 8 carboxylic acid groups.

The ligand design may impart high stability to the coated particles, in biologically relevant conditions, without greatly increasing the particle size or introducing unwanted, non-biocompatible material to the system. Furthermore, the reaction scheme in FIG. 2 allows for a greater number of carboxylate groups to be added to the ligand. FIG. 4 shows the synthesis of a PEG ligand containing 8 carboxylic acid groups ($2^m$, m=3) starting with D (D, is defined in FIG. 2). This methodology would allow the synthesis of a PEG ligand that contains $2^m$ carboxylic acid groups, where m=1, 2, 3, 4 ... etc. For example, each of the 4 amine groups in F can be converted to two more amine groups via reactions 1 and 2, yielding a PEG ligand with 8 amine groups. Each of the 8 amine groups could then be converted to 2 carboxylic acid groups via reactions 3 and 4, to yield a PEG ligand with 16 carboxylic acid groups ($2^m$, m=4). A higher number of carboxylates should provide even tighter binding to the particle surface, allowing the particles to be dispersed at lower pH values.

The ligand may be of interest in the emerging field of nano-biotechnology. Magnetic nanoparticles are used as MRI contrast agents and in bio-separation applications, and are currently being investigated as platforms for targeted drug delivery agents and for use in magnetic field hyperthermia treatment for cancer. Since the resulting nanoparticles are small (average hydrodynamic radius 10 nm) and are stable over a wide pH range and in high ionic strength solutions, this invention has the potential of producing magnetic nanoparticles that can be extremely useful for developing both in vivo and in vitro assays. Conjugation of the magnetic nanoparticles to fluorescent dyes or optically active nanoparticles will allow multi-modal imaging of cells and tissue. Conjugation to proteins or biomolecules of interest will allow analyte separation, imaging and manipulation via external magnetic fields.

The following examples are given to illustrate specific applications. These specific examples are not intended to limit the scope of the disclosure in this application.

EXAMPLE

Compound A (5.1 g) was dissolved in methanol (30 mL), cooled in an ice bath, and stirred under a nitrogen atmosphere. Methyl acrylate (12 mL) in methanol (20 mL) was added dropwise over 30 minutes. The mixture was stirred for 48 hours and the solvent was removed under reduced pressure. The residue was chromatographed on silica gel with 15:1 chloroform:methanol yielding an oil, compound B (R=methyl). Compound B (4.9 g) was dissolved methanol (10 mL) with stirring. Lithium hydroxide (0.34 g) and deionized water (10 mL) were added and the mixture was stirred overnight under a nitrogen atmosphere. Methanol was removed from the mixture under reduced pressure. The aqueous solution was acidified to pH 3-3.5 with 1 M HCl and washed with ethyl acetate and then chloroform. The aqueous solution was saturated with sodium chloride and then extracted with chloroform. The chloroform was dried with sodium sulfate, filtered, and dried under reduced pressure; yielding compound C as a waxy solid.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A compound having the formula:

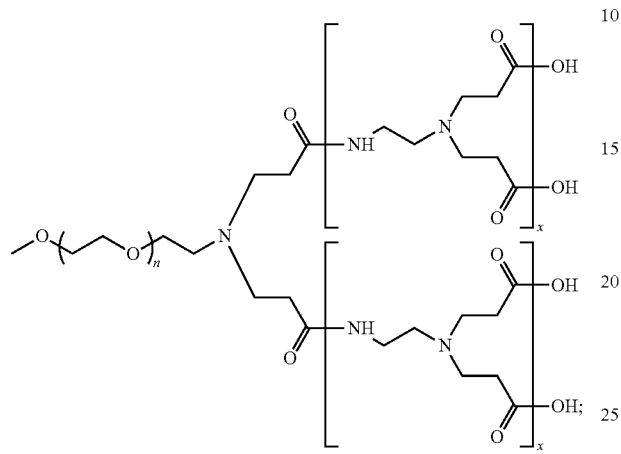

wherein n and x are independently selected positive integers.

2. The compound of claim 1, wherein x is 1, 2, or 3.

3. The compound of claim 2, wherein n is from 10 to 20.

4. The compound of claim 1, wherein n is from 10 to 20.

5. A compound having the formula:

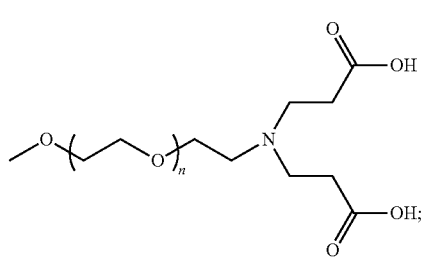

wherein n is a positive integer.

6. The compound of claim 1, wherein n is from 10 to 20.

* * * * *